United States Patent [19]
Lenczycki

[11] 3,981,079
[45] Sept. 21, 1976

[54] DENTAL IMPLANT AND METHOD OF MOUNTING THE SAME IN THE JAW BONE

[76] Inventor: Joseph J. Lenczycki, 89 Florence Road, Riverside, Conn. 06878

[22] Filed: Aug. 23, 1973

[21] Appl. No.: 390,770

[52] U.S. Cl. ............................................... 32/10 A
[51] Int. Cl.² ......................................... A61C 13/00
[58] Field of Search .......................... 32/10 A, 40 R

[56] References Cited
UNITED STATES PATENTS

| | | | |
|---|---|---|---|
| 2,745,180 | 5/1956 | Kiernan, Jr. | 32/10 A |
| 2,857,670 | 10/1958 | Kiernan, Jr. | 32/10 A |
| 3,436,826 | 4/1969 | Edelman | 32/10 A |
| 3,579,831 | 5/1971 | Stevens | 32/10 A |
| 3,866,321 | 2/1975 | Valen | 32/10 A |

*Primary Examiner*—Jack Q. Lever
*Attorney, Agent, or Firm*—Friedman & Goodman

[57] ABSTRACT

A dental implant for maintaining a dental prosthetic device in a fixed relation with respect to a jaw bone includes a support post in the form of an internally threaded hollow cylindrical sleeve. The support post is introduced into a complementay cavity formed in the region of the crest of the jaw bone. The support post is provided with at least partially threaded apertures which are spaced from each other along and angularly displaced from each other about the periphery of the support post. Self-tapping anchoring screws extend through preformed blind holes drilled in the jaw bone with the assistance of a jig forming part of the present invention. The preformed holes extend in a direction substantially normal to the support post and are aligned with the apertures in the latter. The anchoring screws threadedly engage the bone and the threaded portions of the support post without extending beyond the preformed blind holes. In this manner, the anchoring screws anchor and stabilize the support post in the jaw bone. The support post has a free end externally accessible in the region of the crest of the jaw bone for mounting a prosthetic device thereon. A jig and method of mounting the implant in the jaw bone is also described.

17 Claims, 19 Drawing Figures

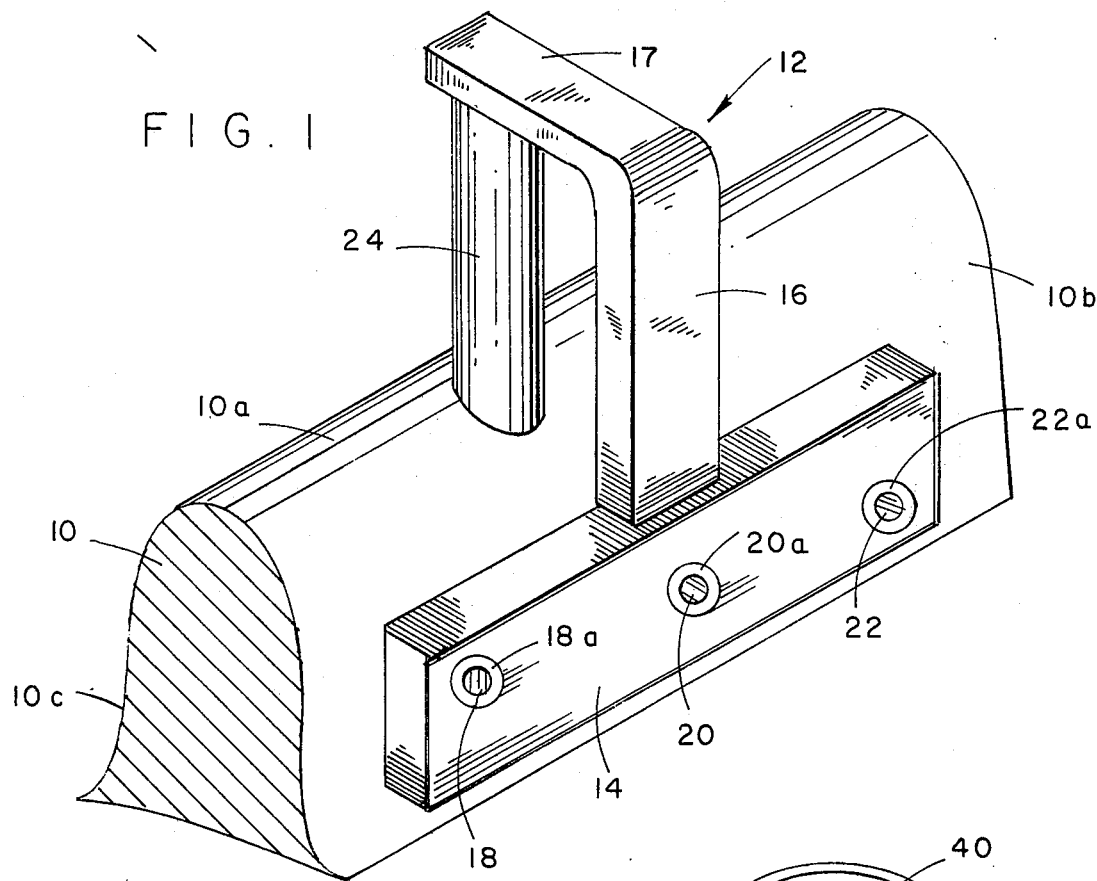
FIG. 1
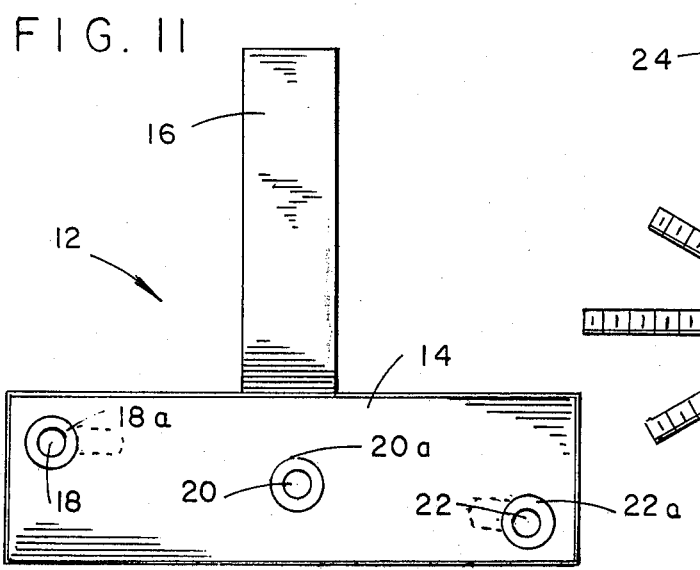
FIG. 11
FIG. 8

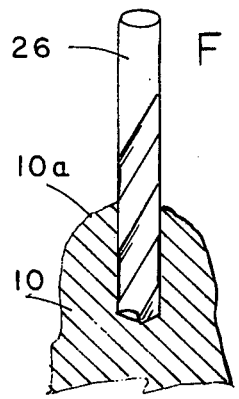
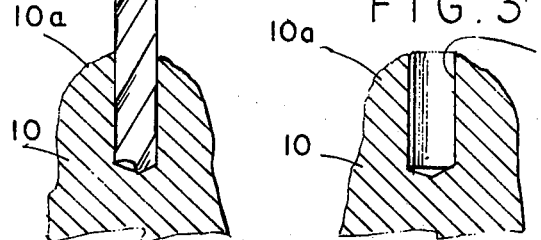
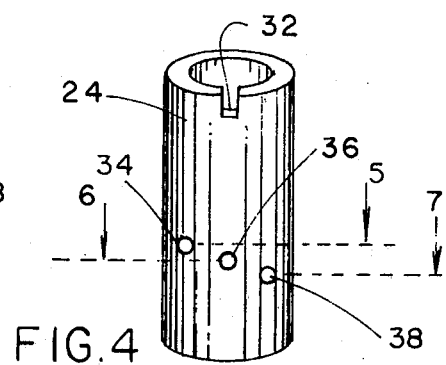
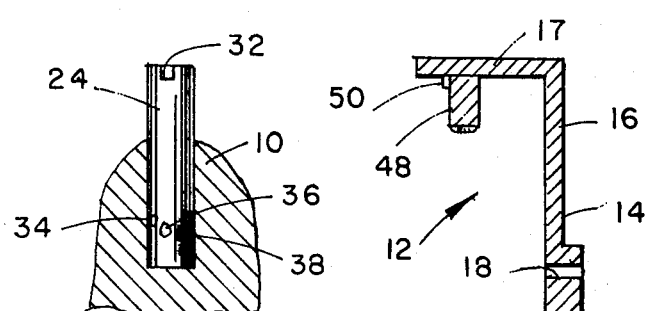
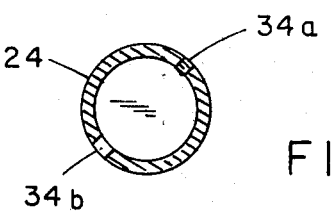
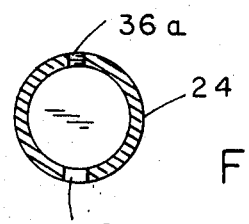
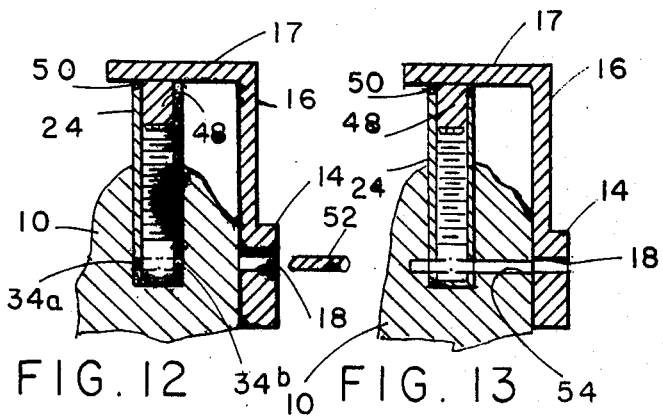
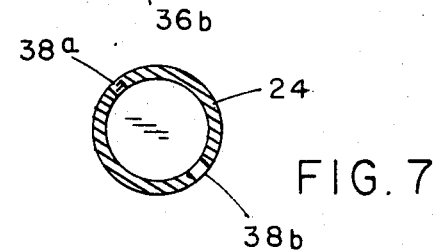
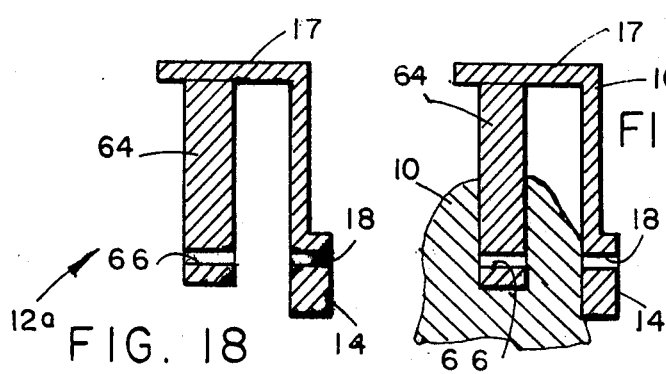
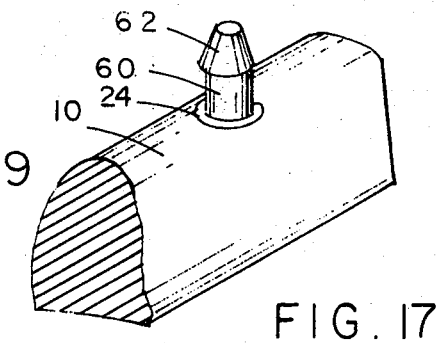

DENTAL IMPLANT AND METHOD OF MOUNTING THE SAME IN THE JAW BONE

BACKGROUND OF THE INVENTION

The present invention generally relates to a dental implant, and more particularly to a bone implant adapted to be received in the jaw bone of the human body, for the purpose of anchoring a desired structure, such as an artificial tooth, to the bone. The present invention also relates to a jig and method of mounting the implant on the jaw bone.

Dental implants of various types are already known. Most of the known dental implants, however, have not been entirely satisfactory for the purposes intended. For example, some implants are in the form of pins, nails or screws which are directly urged into the jaw bone. The disadvantage of these types of implants is that they do not provide sufficient anchorate in the jaw bone under great stresses. Consequently, the danger exists that the implant will, after extended use, become loose from the jaw bone to which it is connected.

According to still other types of known implants, these are in the form of wedge members which are hammered into the jaw bone. The disadvantage with this last type of implants is that all these implants rely for their retention in the jaw bone upon the pressure relationship which exists when the implants are wedged or forced into the jaw bone. However, the jaw bone frequently deteriorates with time and the wedging relationship between the jaw bone and the implants may be lost — sometimes resulting in the implant becoming loose.

Another disadvantage of the known implants is the difficulty and inconvenience of establishing the latter in the jaw bone. The procedures for installing the implants are generally time consuming and uncomfortable to the patient. Implants which provide the possibility of becoming loose only necessitate further dental work at a later time.

According to one dental appliance known in the prior art, an elongate anchoring pin is disposed transversely through the jaw bone. The ends of the anchoring pin continue to project through opposing surfaces of the jaw bone after the implant has been fully mounted thereon. This dental implant has the disadvantage that the extended portions of the transverse anchoring member interfere with the tissues surrounding the jaw bone and interfere with the growth of these tissues at the points where incisions have been made in the flesh covering the jaw bone prior to implantation.

According to another known bone implant, the implant includes a screw which is threaded into the jaw bone and has a free end thereof which remains projecting beyond the jaw bone for fastening any desired structure to the screw. Stabilizing pins are operatively connected to the screw to stabilize the latter to the bone. However, the pins are in the form of nails or stakes which must be hammered into the jaw bone. As suggested above, this procedure may be traumatic to the patient and, at the least, be uncomfortable. Also, the bone implant under discussion frequently results in the pins extending beyond the jaw bone—protruding into the mouth beyond the soft tissues surrounding the jaw bone. The portions of the pin extending into the mouth may interfere with the healing of the tissues as well as possibly forming discomfort to the patient.

SUMMARY OF THE INVENTION

Accordingly, it is an object of the present invention to provide a dental implant assembly which is not possessed of the above described disadvantages associated with prior art dental implants.

It is another object of the present invention to provide a dental implant which is simple in construction and economical to manufacture.

It is another object of the present invention to provide a dental implant which provides sufficient strength and support to the dental prosthetic device which is mounted thereon.

It is yet another object of the present invention to provide a dental implant which more evenly distributes the stresses applied thereon to the surrounding jaw bone instead of concentrating those stresses over relatively small areas.

It is a further object of the present invention to provide a dental implant which is adequately stabilized and anchored to prevent the dislodgement or loosening of the same after extended use.

It is still a further object of the present invention to provide a dental implant which can be securely mounted on the human jaw bone with a minimum of trauma or discomfort to the patient.

It is yet a further object of the present invention to provide a jig for accurately drilling holes in the jaw bone which facilitate both the drilling operation as well as the assembly of the dental implant.

It is an additional object of the present invention to provide a dental implant which minimizes the extent to which portions of the implant extend beyond the jaw bone to interfere with the growth or healing of the tissue surrounding the jaw bone.

It is still an additional object of the present invention to provide a method for establishing properly anchored and stabilized dental implants in complementary cavities formed in a jaw bone.

In order to achieve the above objects, as well as others which will become apparent hereafter, the dental implant assembly for maintaining a dental prosthetic device in fixed relation with respect to a jaw bone comprises a support post adapted to be introduced into a complementary cavity formed in the region of the crest of the jaw bone. Said support post is provided with at least one transverse aperture formed therein at an end of said support post adapted to be disposed within said cavity. At least one anchoring screw is provided which is adapted to extend through a blind hole drilled in the jaw bone in a direction substantially normal to said support post to threadedly engage the jaw bone and said transverse aperture formed in said support post. In this manner, said anchoring screw anchors and stabilizes the support post in the jaw bone.

In accordance with the presently preferred embodiment, said support post is in the form of a hollow cylindrical sleeve which is provided with an internal thread adapted to threadedly engage a threaded shank adapted to support a prosthetic device. Further, a plurality of transverse apertures are advantageously provided each adapted to receive another anchoring screw, said transverse apertures being spaced from each other along said support post. Said transverse apertures are further advantageously angularly displaced from one another about said support post.

The anchoring screw in accordance with the present invention is advantageously self-tapping and is provided with an enlarged free end in the form of a finger grip to facilitate threadedly advancing said anchoring screw through the jaw bone in said tranverse hole.

A jig for drilling holes in the jaw bone in accordance with the present invention comprises a skirt adapted to be positioned adjacently to the jaw bone laterally of the cavity. Said skirt is provided with at least one guide hole adapted to guide a drill bit through the jaw bone towards the cavity in a direction generally normal to the direction of the cavity. A neck portion extends from said skirt and has at least a portion thereof facing or overlying the exposed open end of the cavity. Pin means is provided which projects from said neck portion towards said cavity for engaging the guide post and aligning said at least one guide hole in said skirt with a corresponding aperture in the support post prior to drilling the holes in the jaw bone. Where the support post has the free end thereof disposed in the region of the crest of the jaw bone, said pin means is provided with alignment means adapted to engage the free end of the support post and angularly position said skirt about the support post to align said at least one guide hole with a corresponding aperture in the support post. The alignment means comprises a notch in the support post adapted to receive a mating alignment tab of the jig.

According to a variation of the jig, said pin means projects from said neck portion towards said cavity and is adapted to be received in the latter. In this case, said pin means includes at least one hole aligned with said at least one guide hole and corresponds to a corresponding aperture in the support post. In this manner, a hole can be drilled in the jaw bone in alignment with said guide hole in said skirt and holes in said pin means which is aligned with a corresponding aperture in the support post subsequently positioned in the cavity.

A method of the present invention comprises the step of drilling a hole into the crest of the jaw bone in a first direction to form a cavity in the jaw bone having an accessible open end. A blind transverse hole is drilled in the jaw bone which communicates with the cavity and is directed in a second direction substantially normal to said first direction. An apertured support post is inserted into the cavity through said accessible open end with the aperture therein aligned with a transverse hole drilled in the jaw bone. An anchoring screw is threaded through the hole in the jaw bone as well as through the aperture in the support post.

In the presently preferred method, a plurality of transverse holes are drilled in the jaw bone in alignment with corresponding holes in the support post and a plurality of threaded screws are threaded through the transverse holes and through the corresponding apertures in the support post.

Where the apertured post is inserted into the cavity prior to the drilling of said at least one transverse hole in said second direction, a jig is engaged with the support post, the dental jig being provided with at least one guide hole aligned with a corresponding aperture in the support post. The drilling operation comprises the step of advancing a drill bit through said at least one guide hole. The transverse hole drilled into the second direction is drilled to only penetrate one surface of the jaw bone. In this manner, a blind hole is formed. Said anchoring screw is threadedly advanced without extending beyond said blind hole.

BRIEF DESCRIPTION OF THE DRAWINGS

With the above and additional objects and advantages in view, as will hereinafter appear, this invention comprises the devices, combinations and arrangements of parts hereinafter described and illustrated in the accompanying drawings of a preferred embodiment in which:

FIG. 1 is a perspective view of a portion of a jaw bone and a dental jig cooperating with a support post of the dental implant in accordance with the present invention, showing the relationship between the jaw bone, jig and dental implant during the mounting procedure;

FIG. 2 is a cross-section of the jaw bone shown in FIG. 1, showing a drill bit drilling a hole through the crest of the jaw bone to form a support post receiving cavity;

FIG. 3 is similar to FIG. 2 and shows the cavity formed by the drilling operation of FIG. 2;

FIG. 4 is a perspective view of an apertured support post in accordance with the present invention, illustrating a plurality of spaced anchoring screw receiving apertures and an alignment notch;

FIGS. 5–7 are cross-sections of the support post taken along lines 5, 6 and 7 respectively in FIG. 4;

FIG. 8 is an enlarged perspective view of the support post shown in FIG. 4, further schematically illustrating the manner in which anchoring screws are adapted to extend through the support post;

FIG. 9 is a cross-section similar to FIGS. 2 and 3, showing the support post of FIG. 4 disposed in the cavity shown in FIG. 3;

FIGS. 10 and 11 are respectively a cross side elevational view and front elevational view of a jig in accordance with the present invention which facilitates the drilling of aligned holes through the jaw bone for receiving threaded anchoring screws;

FIG. 12 is a cross-section similar to FIG. 10, showing the jig of FIGS. 10 and 11 cooperating with the support post and providing guide holes aligned with the apertures in the support post;

FIG. 13 is similar to FIG. 12, showing the hole drilled in the jaw bone with the assistance of the jig;

FIG. 17 is a perspective view of the jaw bone, shown with the portion of the support post projecting above the jaw bone severed substantially flush with the crest of the jaw bone, and further showing a shank provided with a head or coping portion thereon adapted to support a prosthetic device;

FIGS. 18 and 19 are similar to FIGS. 10 and 12, but showing a further embodiment of the jig shown in FIGS. 10 and 11.

DETAILED DESCRIPTION OF THE PREFERRED EMBODIMENTS

Figure 14:
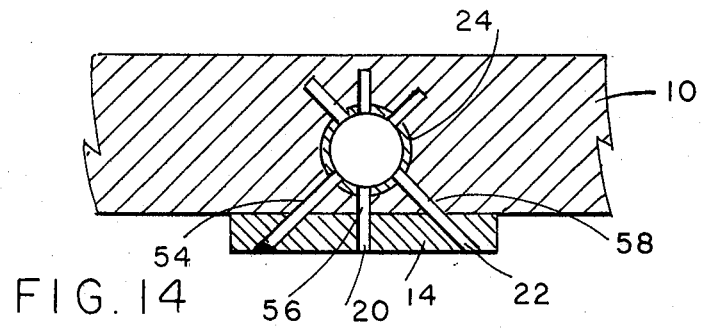
FIG. 14 is a top plan cross-sectional view of the jaw bone and of the jig, taken at different elevations along the support post to illustrate the angular displacement between the spaced holes drilled through the jaw bone.

Referring now to the drawings, in which similar or identical parts have been designated by the same reference numerals throughout, and first referring to FIG. 1, a section of a jaw bone is generally designated by reference numeral 10. The jaw bone will be described as having a crest 10d and facial and lingual surfaces 10b and 10c respectively.

A guide or jig 12, utilized to facilitate the mounting of the implant, to be described, comprises an elongate skirt 14 in the form of a bar or plate. Projecting from the skirt 14 is a neck portion 16 which is shown to be substantially normal to the skirt 14. The neck portion 16 includes an overhanging member 17 which overlies the crest 10a of the jaw bone. The length of the neck 16 is selected based on considerations which will become apparent hereafter.

The skirt 14 is provided with guide holes 18, 20 and 22 whose specific positions and orientations will be further described below. In the presently preferred embodiment, each guide hole is lined with a bearing sleeve or bushing 18a, 20a and 22a respectively.

A mounting post 24, forming part of the dental implant, is shown to extend from the crest 10a and engage the overhanging member 17. The specific construction of the dental implant as well as the method of mounting the same on the jaw bone 10 will now be specifically described.

Referring to FIGS. 2 and 3, the method of mounting an implant in accordance with the present invention comprises the step of drilling, with any conventional drill bit 26, a hole or a cavity 28 in the region of the crest 10a of the jaw bone 10. As best depicted in FIG. 3, the resulting cavity 28 is in the nature of a blind hole whose depth is selected in accordance with considerations which will become apparent hereafter. The diameter of the drill hole 28 is selected to produce a cavity 28 which matingly receives with close tolerance the mounting post 24.

Referring to FIGS. 4–7, the details of the support post 24 are shown. As above suggested, the post 24 in accordance with one presently preferred embodiment is hollow and in the form of a cylindrical sleeve. The post 24 is provided with an alignment notch 32 whose function will be described hereafter.

The post 24 is provided with at least one, but preferably a plurality of apertures. In the embodiment being described, three apertures 34, 36 and 38 are provided. The hollow post 24 is generally elongate and the apertures 34, 36 and 38 are spaced from each other along the length or axis of the support post 24. Further, the apertures are angularly disposed about the axis of the support post. As best shown in FIG. 4, the apertures or holes 34, 36 and 38 are successively spaced in substantially equal or graduated increments.

Transverse cross-sections through the hollow post 24 at different elevations corresponding to the positions of the apertures 34, 36 and 38 depict the nature of the apertures. When the apertures are formed in a hollow sleeve of the type being described, the apertures are formed in diametrically opposed wall portions of the hollow post. Threaded aperture portions 34a, 36a and 38a are provided in the trailing wall portions while unthreaded aperture portions 34b, 36b and 38b are provided in the leading wall portions. Entering screws, to be described, first enter the unthreaded hole portions and subsequently threadedly mesh the threaded hole portions.

Referring to FIG. 8, an internal thread 40 is shown formed on the interior surface of the support post 24. The thread 40 is adapted to threadedly engage a shank of a prosthetic supporting device, as to be described in connection with FIG. 17.

FIG. 8 further schematically shows the manner in which anchoring screws 42, 44 and 46 extend through the respective apertures 34, 36 and 38. The anchoring screws are advantageously self-tapping screws which can, with advancement thereof, form an internal thread in the jaw bone 10. As suggested above, the unthreaded hole portions 34b, 36b and 38b are selected to have sufficiently large diameters to permit free passage of the anchoring screws. On the other hand, the anchoring screws are adapted to threadedly engage the threaded apertures or holes 34a, 36a and 38a.

Referring to FIG. 9, the support post 24 is inserted into the cavity 28 with the apertures 34, 36 and 38 disposed within the cavity while the notch 32 extends beyond the cavity. In the presently preferred embodiment, the length of the support post 24 is selected to be longer than the length of the cavity 28 to thereby project or extend beyond the crest 10a of the jaw bone. However, it is not critical for the purposes of achieving the object of the present invention that the support post 24 project beyond the crest of the jaw bone when fully received within the cavity 28. The reason for this will become apparent hereafter.

Referring to FIGS. 10 and 12, the overhanging member 17 is shown to be provided with a pin 48 which, advantageously, has a tapered free end. The diameter of the pin 48 is selected to correspond to the internal diameters of the thread 40 to thereby be matingly receivable within the hollow portion of the support post 24 with small tolerance therebetween. The tapered free end of the pin 48 facilitates insertion of the pin within the support post 24, as suggested in FIG. 12.

Provided in the region of the pin 48 where the latter projects from the overhanging member 17 is an alignment tab 50 whose configuration is selected to correspond to that of the alignment notch 32 in the support post. The alignment tab 50 is rigidly affixed to the overhanging member relative to the axis of the pin 48.

When the jig 12 is positioned for use, the pin 48 is slidingly inserted within the hollow support post 24 and the skirt 14 and neck 16 are angularly turned about the axis of the support post 24 and pin 48 to bring the tab 50 into alignment with the notch 32. When such alignment has been achieved, the pin 48 is caused to further penetrate within the support post while the alignment tab 50 is simultaneously received within the notch 32.

The angular position of the notch 32 about the periphery of the support post 24, as well as the angular position of the alignment tab 50 about the periphery of the pin 48 are selected so that alignment of the notch 32 and the tab 50 brings the apertures 34, 36 and 38 into alignment with respective guide holes 18, 20 and 22.

As should now be clear, for the guide holes 18, 20 and 22 to be alignable with the apertures 34, 36 and 38 respectively the guide holes must be similarly spaced from one another in the axial direction of the support post. Further, the guide holes must be angularly disposed one with respect to the other to converge upon the support post at angles corresponding to respective angles included between the apertures in the support post.

In FIGS. 12 and 13, a drill bit 52 is schematically illustrated to indicate the manner of formation of transverse holes within the jaw bone 10. It should be noted that the resulting drilled hole 54 is directed substantially normally to the axis of the support post 24.

While the above description has suggested that the skirt 14 be disposed on the lingual side along the lingual surface 10b of the jaw bone, this is, clearly, not a critical feature of the present invention and the skirt 14 can also be disposed on the facial side 10c to thereby initiate the transverse hole from that side. However, according to the presently preferred embodiment, the drilled hole 54 is a blind hole which penetrates only one surface of the jaw bone.

While only one drilled hole 54 is shown, it should be clear that a comparable drilled hole is drilled for each of the apertures 34, 36 and 38 formed in the support post 24.

The bit 52 is guided by one of the respective guide holes 18, 20 or 22. Once so guided, the drill bit 52 drills the hole 54 in the jaw bone 10 and is received in the unthreaded aperture portion of the support post. The inside diameters of the threads formed in the threaded hole portions 34a, 36a and 38a are selected to be sufficiently large to permit the drill bit 52 to pass therethrough without damaging the thread. In this manner, the drill bit may advance beyond the threaded hole portions to extend the drilled holes beyond the support post.

The diameter of the drill bit 52 is selected to be sufficiently small to permit the anchoring screws 42, 44 and 46 to provide their own thread as the screws advance through the jaw bone.

Referring to FIG. 14, the three transverse holes 54, 56 and 58 formed by advancing the drill bit successively through the associated guide holes and apertures in the support post, are illustrated schematically. In actuality, in the presently preferred embodiment, the drilled holes are at different elevational levels along the support post to correspond with the axial spacings of the apertures, as suggested in FIG. 4. The drilling or guide jig 12 is now removed by withdrawing the pin 48 from the support post 24.

Figure 15:
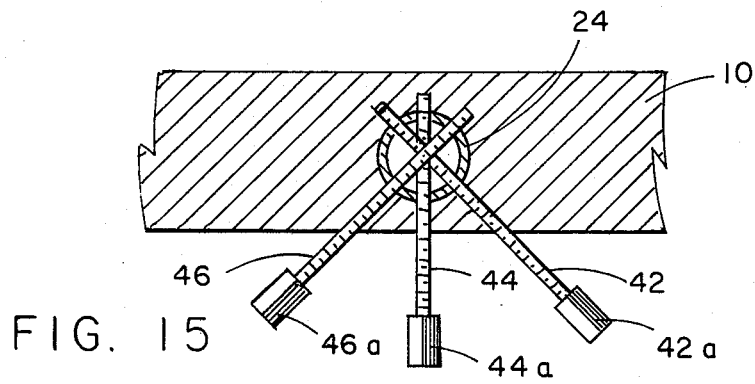
FIG. 15 is similar to FIG. 14, showing the manner in which the anchoring screws are threadedly engaged with the jaw bone and the support post.

In FIG. 15, the anchoring screws 42, 44 and 46 are shown fully engaged or threadedly received in both the jaw bone 10 as well as in the support post 24.

Each of the anchoring screws is provided with an enlarged plastic head 42a, 44a and 46a respectively to form a finger grip which can be gripped and turned to advance the anchoring screws through the drilled holes and into the support post.

Figure 16:
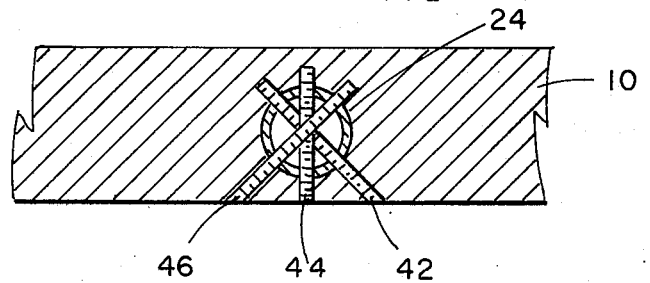
FIG. 16 is similar to FIG. 15, showing the manner in which the free ends of the anchoring screws are severed to substantially prevent the screws from extending beyond the external surface of the jaw bone.

Advantageously, the lengths of the anchoring screws are selected to be oversized to thereby extend beyond the external surface of the jaw bone 10 when fully threadedly engaged. This facilitates manipulation of the anchoring screws. As shown in FIG. 16, the anchoring screws are advantageously severed as closely as possible and preferably flush with the penetrated surface of the jaw bone. With such an arrangement, the support post 24 is fully stabilized within the cavity 28.

Referring to FIGS. 9 and 17, it is noted that the support post 24 projects beyond the crest 10a of the jaw bone. With such an oversized length of the support post, the portion projecting beyond the crest is advantageously severed as close as possible to the surface of the jaw bone and advantageously flush therewith or with such projection as is desired. With the support post 24 securely mounted and held within the jaw bone, a thread of the shank 60 is now receivable within the support post 24. The shank 60 may be provided with any conventional head or coping portion 62 suitable for supporting or being connected to a prosthetic device.

It should be noted that the dental implant of the present invention firstly minimizes the number of protuberances or projections exteriorly of the jaw bone which the soft tissues around the jaw bone come into contact with. Further, the stresses applied to the jaw bone are not concentrated but are distributed by the spaced and angularly displaced anchoring screws. Of considerable importance is that the insertion of the dental implant merely requires the drilling of a small number of holes in the jaw bone and does not require the hammering of pointed objects into the jaw bone as frequently required with comparable prior art implants. Consequently, the present implant minimizes or reduces the amount of trauma to which the patient is exposed. As suggested above, the minimal number of protuberances or members which project beyond the jaw bone furthers the healing or growing process of the soft tissues around the jaw bone. Stabilization of the various elements or components of the implant, which cannot be overemphasized in the proper healing of the soft tissues, is further enhanced by the roughened or threaded surface of the anchoring screws. By permitting the bone to grow around the screw threads, the screw threads are themselves stabilized within the jaw bone, this insuring the continued stabilization of the support post. To this end, it is possible to provide additional perforations or apertures in the support post 24 which are not adapted to receive anchoring screws. Instead, the perforations in the support post can be provided to permit the bone to grow through the perforations and into the support post, this further stabilizing the support post.

While the support post 24 has been shown and described as a hollow cylindrical sleeve, this is not a critical feature of the present invention. Alternately, the support post 24 can be solid and incorporate the head or coping portion thereon. When using the alternate type of support post, a jig 12a as shown in FIG. 18 can be utilized. The jig 12a includes an elongate rod 64 which is longer than the pin 48. The rod 64 extends sufficiently from the overhanging member 17 to have a free end portion coextensive with the guide holes provided in the skirt 14. Unthreaded holes 66 are provided in the rod 64 which are aligned with respective ones of the guide holes in the skirt and correspond to the apertures in the solid or hollow support post.

With the jig 12a, after the cavity 28 has been drilled, the rod 64 is inserted therein as shown in FIG. 19. The steps above described in connection with FIGS. 12 and 13 are now repeated to provide the transverse drilled hole in the jaw bone. After the holes have been drilled, the jig 12a is removed and a support post, hollow or solid, is inserted into the cavity and provided with apertures which correspond with the holes 66 formed in the rod 64. The support post is turned about its axis to bring the apertures therein into alignment with the drilled transverse holes at which time the anchoring screws are threadedly inserted as above described.

Numerous alterations of the structure herein disclosed will suggest themselves to those skilled in the art. However, it is to be understood that the present disclosure relates to a preferred embodiment of the invention which is for the purposes of illustration only and is not to be construed as a limitation of the invention.

What is claimed is:

1. Dental implant assembly for maintaining a dental prosthetic device in fixed relation with respect to a jaw bone, the implant assembly comprising a support post adapted to be introduced into a complementary cavity formed in the region of the crest of the jaw bone, said support post being provided with at least one transverse aperture formed therein at an end of said support post adapted to be disposed within said cavity; at least one anchoring screw adapted to extend through a hole drilled in the jaw bone in a direction substantially normal to said support post to threadedly engage the jaw bone and said transverse aperture formed in said support post, whereby said anchoring screw anchors and stabilizes said support post in the jaw bone; said support post being formed as a hollow cylindrical sleeve; and said at least one transverse aperture being formed through diametrically opposed wall portions of said sleeve, the aperture formed in the leading wall portion through which the anchoring screw first advances being unthreaded, and the aperture formed in the trailing wall portion into which the anchoring screw subsequently advances being threaded to threadedly receive said anchoring screw.

2. Dental implant assembly as defined in claim 1, wherein said sleeve is provided with an internal thread adapted to threadedly engage a threaded shank adapted to support a prosthetic device.

3. Dental implant assembly as defined in claim 1, wherein a plurality of transverse apertures are provided each adapted to receive another transverse anchoring screw, said transverse apertures being spaced from each other along said support post.

4. Dental implant assembly as defined in claim 3, wherein said transverse apertures are angularly displaced from one another about said support post.

5. Dental implant assembly as defined in claim 1, wherein said anchoring screw is self-threading.

6. Dental implant assembly as defined in claim 1, wherein said anchoring screw is provided with an enlarged free end to form a finger grip to facilitate threadedly advancing said anchoring screw through the jaw bone and said transverse aperture.

7. Dental implant assembly as defined in claim 1, wherein said anchoring screw has an oversized length and is adapted to be cut flush with the jaw bone subsequent to desired advancement into the latter.

8. Dental implant assembly as defined in claim 1, wherein said support post has an oversized length and extends exteriorly of the cavity, said support being adapted to be cut substantially flush with the crest of the jaw bone.

9. Dental implant assembly as defined in claim 1, wherein said support post has a free end thereof disposed in the region of the crest of the jaw bone, said free end being provided with alignment means adapted to engage a jig.

10. Dental implant assembly as defined in claim 9, wherein said alignment means comprises a notch adapted to receive a mating alignment tab of the jig.

11. A method of inserting a dental implant into a jaw bone comprising the steps of drilling a hole into the crest of the jaw bone in a first direction to form a cavity in the jaw bone having an accessible open end; drilling at least one hole in the jaw bone communicating with the cavity in a second direction substantially normal to said first direction; inserting an apertured support post into the cavity through said accessible open end with the aperture therein aligned with the hole drilled in the jaw bone; and threading an anchoring screw through the hole in the jaw bone as well as through the aperture in the screw post; the step of inserting the apertured post into the cavity preceding the step of drilling said at least one hole in said second direction.

12. A method as defined in claim 11, wherein a plurality of transverse holes are drilled in the jaw bone in alignment with corresponding holes in the support post.

13. A method as defined in claim 12, wherein a plurality of threaded screws are threaded through the transverse holes in the jaw bone and through the corresponding apertures in the support post.

14. A method as defined in claim 11, wherein said step of drilling said at least one hole in said second direction comprises the step of engaging a jig with the support post, the jig being provided with at least one guide hole aligned with said hole in said second direction and a corresponding aperture in the support post; and advancing a drill bit through said at last one guide hole.

15. A method as defined in claim 11, wherein the support post is oversized to extend beyond the crest of the jaw bone, the method further comprising the step of severing substantially the portion of the support post which extends beyond the crest.

16. A method as defined in claim 11, wherein said at least one hole in the jaw bone is drilled to only penetrate one surface of the jaw bone, whereby a blind hole is formed, said anchoring screw threadedly advancing without extending beyond said blind hole.

17. A method of inserting a dental implant into a jaw bone comprising the steps of drilling a hole into the crest of the jaw bone in a first direction to form a cavity in the jaw bone having an accessible open end; drilling at least one hole in the jaw bone communicating with the cavity in a second direction substantially normal to said first direction; inserting an apertured support post into the cavity through said accessible open end with the aperture therein aligned with the hole drilled in the jaw bone; threading an anchoring screw through the hole in the jaw bone as well as through the aperture in the screw post, the anchoring screw being oversized and extending beyond the jaw bone when fully threaded into the latter; and severing substantially a portion of the support post which extends beyond the jaw bone to be flush therewith.

* * * * *